United States Patent [19]

Fröstl et al.

[11] Patent Number: 5,204,334

[45] Date of Patent: Apr. 20, 1993

[54] BENZOHETEROCYCLYLALK-YLAMINOALKANEDIPHOSPHONIC ACIDS, COMPOSITIONS THEREOF, AND USE THEREOF IN THE TREATMENT OF CALCIUM METABOLISM DISORDERS

[75] Inventors: Wolfgang Fröstl; Knut A. Jaeggi, both of Basel, Switzerland

[73] Assignee: Ciba-Geigy Corporation, Ardsley, N.Y.

[21] Appl. No.: 765,360

[22] Filed: Sep. 25, 1991

[30] Foreign Application Priority Data

Oct. 18, 1990 [CH] Switzerland .................. 3332/90

[51] Int. Cl.$^5$ ..................... A61K 31/67; C07F 9/38
[52] U.S. Cl. ..................... 514/96; 514/100; 549/5; 549/6; 549/7; 549/220
[58] Field of Search ............ 519/5, 6, 7, 220; 514/96, 97, 100, 101

[56] References Cited

U.S. PATENT DOCUMENTS

| | | | |
|---|---|---|---|
| 4,473,560 | 9/1984 | Biere et al. | 549/6 |
| 4,503,049 | 3/1985 | Biere et al. | 514/80 |
| 4,687,767 | 8/1987 | Bosies et al. | 514/89 |
| 4,761,406 | 8/1988 | Flora et al. | 514/89 |
| 4,777,163 | 10/1988 | Bosies et al. | 514/97 |
| 4,784,993 | 11/1988 | Bosies et al. | 514/93 |
| 4,871,720 | 10/1989 | Jaeggi | 514/89 |
| 4,933,472 | 6/1990 | Takeuchi | 514/89 |
| 5,013,725 | 5/1991 | Takeuchi | 514/89 |
| 5,110,807 | 5/1992 | Jaeggi | 514/89 |

FOREIGN PATENT DOCUMENTS

| | | |
|---|---|---|
| 0084822 | 8/1983 | European Pat. Off. . |
| 0085321 | 8/1983 | European Pat. Off. . |
| 0170228 | 2/1986 | European Pat. Off. . |
| 0337706 | 10/1989 | European Pat. Off. . |

*Primary Examiner*—Richard L. Raymond
*Assistant Examiner*—Mark W. Russell
*Attorney, Agent, or Firm*—Irving M. Fishman; Karen G. Kaiser

[57] ABSTRACT

Benzoheterocyclylalkylaminoalkanediphosphonic acids of formula I

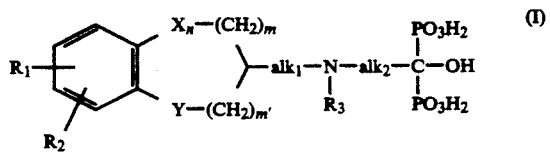

wherein $R_1$ and $R_2$, independently of one another, are hydrogen, lower alkyl, lower alkoxy, halogen or trifluoromethyl, $R_3$ is hydrogen or lower alkyl, X and Y, independently of one another, are oxy or thio, $alk_1$ and $alk_2$ are identical or different lower alkylene radicals, n is 0 or 1 and m and m', independently of one another, are 0, 1 or 2, the sum of n, m and m' being 1, 2 or 3, and their salts exhibit a pronounced regulatory action on the calcium metabolism of warm-blooded animals. They are prepared, for example, as follows: in a compound of the formula

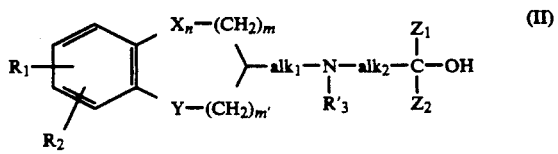

wherein $R_1$, $R_2$, n, m, m', X, Y, $alk_1$ and $alk_2$ are as defined above, $R'_3$ is one of the groups $R_3$ mentioned above or is an amino-protecting group $R_0$, $Z_1$ is a functionally modified phosphono group, and $Z_2$ is a free or functionally modified phosphono group, converting functionally modified phosphono $Z_1$ and, where appropriate, $Z_2$ into the free phosphono group, and, if desired, converting a resulting compound into a different compound of formula I, separating a mixture of isomers obtainable in accordance with the process into the components and separating the preferred isomer, and/or converting a free compound obtainable in accordance with the process into a salt or converting a salt obtainable in accordance with the process into the corresponding free compound.

20 Claims, No Drawings

BENZOHETEROCYCLYLALKYLAMINOALK-ANEDIPHOSPHONIC ACIDS, COMPOSITIONS THEREOF, AND USE THEREOF IN THE TREATMENT OF CALCIUM METABOLISM DISORDERS

The invention relates to novel benzoheterocyclylalkylaminoalkanediphosphonic acids of formula I

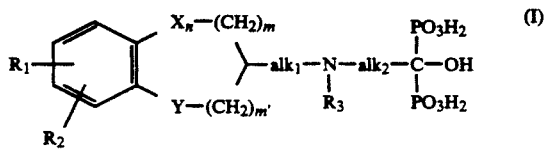

wherein $R_1$ and $R_2$, independently of one another, are hydrogen, lower alkyl, lower alkoxy, halogen or trifluoromethyl, $R_3$ is hydrogen or lower alkyl, X and Y, independently of one another, are oxy or thio, $alk_1$ and $alk_2$ are identical or different lower alkylene radicals, n is 0 or 1 and m and m', independently of one another, are 0, 1 or 2, the sum of n, m and m' being 1, 2 or 3, and their salts, to processes for the preparation of the mentioned compounds, to pharmaceutical compositions comprising those compounds and to their use as active ingredients in medicaments.

The benzoheterocyclyl radical of the formula

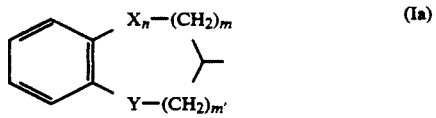

is, for example, 2,3-dihydrobenzofuranyl or 2,3-dihydrobenzothienyl (Y=oxy or thio; n=0; m=1 and m'=0 or m=0 and m'=1), chromanyl or thiochromanyl (Y=oxy or thio; n=0; m and m'=1 or m=0 and m'=2 or m=2 and m'=0), 1,4-benzodioxanyl (X and Y=oxy; n=1; m=0 and m'=1 or m=1 and m'=0); 1,4-benzoxathianyl (X=oxy and Y=thio or X=thio and Y=oxy; n=1; m=0 and m'=1 or m=1 and m'=0); 1,4-benzodithianyl (X and Y=thio; n=1; m=0 and m'=1 or m=1 and m'=0); 2,3,4,5-tetrahydrobenzoxepinyl or 2,3,4,5-tetrahydrobenzothiepinyl (Y=oxy or thio; n=0; m=0 and m'=3 or m=1 and m'=2 or m=2 and m'=1 or m=3 and m'=0), 2,3,4,5-tetrahydrobenzodioxepinyl (X and Y=oxy; n=1; m=0 and m'=2 or m and m'=1 or m=2 and m'=0), 2,3,4,5-tetrahydrobenzoxathiepinyl (X=oxy and Y=thio or X=thio and Y=oxy; n=1; m=0 and m'=2 or m and m'=1 or m=2 and m'=0) or 2,3,4,5-tetrahydrobenzodithiepinyl (X and Y=thio; n=1; m=0 and m'=2 or m and m'=1 or m=2 and m'=0). The mentioned radicals may be unsubstituted or monosubstituted by a radical $R_1$ other than hydrogen or disubstituted by identical or different radicals $R_1$ and $R_2$.

Preference is given to 2,3-dihydrobenzofuranyl, especially 2,3-dihydrobenzofuran-2-yl, chromanyl, especially chroman-3-yl, 1,4-benzodioxanyl, especially 1,4-benzodioxan-2-yl, 6-lower alkyl-, 6-lower alkoxy- and 7-halo-1,4-benzodioxan-2-yl.

Hereinbefore and hereinafter, lower radicals and compounds are to be understood as being, for example, radicals and compounds having up to and including 7, preferably up to and including 4, carbon atoms (C atoms).

Lower alkyl is, for example, $C_1$–$C_7$alkyl, preferably $C_1$–$C_4$alkyl, such as, especially, methyl or, secondly, ethyl, propyl, isopropyl or butyl, but may also be isobutyl, sec-butyl, tert-butyl or a $C_5$–$C_7$alkyl group, such as pentyl, hexyl or heptyl group.

Lower alkylene is, for example, $C_1$–$C_7$alkylene, especially $C_1$–$C_7$alkylene; in the case of $alk_1$ especially $C_1$–$C_4$alkylene, such as methylene, ethylene, 1,3-propylene or 1,4-butylene, and in the case of $alk_2$ especially $C_2$–$C_3$alkylene, such as ethylene or, secondly, 1,3-propylene.

Lower alkoxy is, for example, $C_1$–$C_7$alkoxy, preferably $C_1$–$C_4$alkoxy, such as methoxy, ethoxy, propoxy, isopropoxy or butoxy, but may also be isobutoxy, sec-butoxy, tert-butoxy or a pentyloxy, hexyloxy or heptyloxy group.

Halogen is, for example, halogen having an atomic number of up to and including 35, such as chlorine or fluorine, and also bromine.

Salts of compounds of formula I are, for example, salts thereof with pharmaceutically acceptable bases, such as non-toxic metal salts derived from metals of groups Ia, Ib, IIa and IIb, for example alkali metal salts, especially sodium or potassium salts, alkaline earth metal salts, especially calcium or magnesium salts, copper, aluminum or zinc salts, also ammonium salts with ammonia or organic amines or quaternary ammonium bases, such as free or C-hydroxylated aliphatic amines, especially mono-, di- or tri-lower alkylamines, for example methyl-, ethyl- or diethyl-amine, mono-, di- or tri-(hydroxy-lower alkyl)amines, such as ethanol-, diethanol- or triethanol-amine, tris(hydroxymethyl)methylamine or 2-hydroxy-tert-butylamine, or N-(hydroxy-lower alkyl)-N,N-di-lower alkylamines or N-(polyhydroxy-lower alkyl)-N-lower alkylamines, such as 2-(dimethylamino)ethanol or D-glucamine, or quaternary aliphatic ammonium hydroxides, for example tetrabutylammonium hydroxide. Both complete salts and partial salts, that is to say, salts having 1, 2, 3 or 4, preferably 2, equivalents of base per mole of acid of formula I, are included.

For isolation or purification purposes it is also possible to use pharmaceutically unsuitable salts. Only the pharmaceutically acceptable, non-toxic salts are used therapeutically and these salts are therefore preferred.

The compounds of formula I and their salts have valuable pharmacological properties. In particular, they exhibit a pronounced regulatory action on the calcium metabolism of warm-blooded animals. For example, in rats, they bring about pronounced inhibition of bone resorption, which can be demonstrated both in the experimental procedure according to Acta Endocrinol. 78, 613–24 (1975) and by reference to the PTH-induced increase in the serum calcium level after subcutaneous administration in doses of from approximately 0.01 to approximately 1.0 mg/kg, and in the TPTX (thyroparathyroidectomised) rat model by reference to the experimental hypercalcaemia, induced by vitamin $D_3$, after the administration of doses of from approximately 0.0005 to approximately 0.5 mg/kg s.c. and in some cases also p.o.. The tumour hypercalcaemia induced by Walker-256-tumours is likewise inhibited after peroral administration of from approximately 1.0 to approximately 100 mg/kg. Further, in adjuvant arthritis in rats in the experimental procedure according to Newbold, Brit. J. Pharmacology 21, 127 (1963) and according to Kaibara et al., J. Exp. Med. 159, 1388-96 (1984), they exhibit a marked inhibition of the progression of chronic arthritic processes in doses of from approximately 0.01 to approximately 1.0 mg/kg s.c.. The most suitable indications are tumour-induced hypercalcaemia, bone metastases and Paget's disease.

The compounds of formula I and their salts are therefore eminently suitable as active ingredients in medicaments for the treatment of diseases that can be attributed to calcium metabolism disorders, especially tumour-induced hypercalcaemia, of bone metastases and Paget's disease, and of inflammatory processes in joints, degenerative processes in the articular cartilage, or osteoporosis, periodontitis, hyperparathyroidism and of calcium deposits in blood vessels or in prosthetic implants.

The invention relates especially to compounds of formula I wherein $R_1$ and $R_2$, independently of one another, are hydrogen, lower alkyl, lower alkoxy, halogen or trifluoromethyl, $R_3$ is hydrogen or lower alkyl, the benzoheterocyclyl radical of formula Ia is 2,3-dihydrobenzofuranyl, 2,3-dihydrobenzothienyl, chromanyl, thiochromanyl, 1,4-benzodioxanyl, 1,4-benzoxathianyl, 1,4-benzodithianyl, 2,3,4,5-tetrahydrobenzoxepinyl, 2,3,4,5-tetrahydrobenzothiepinyl, 2,3,4,5-tetrahydrobenzodioxepinyl, 2,3,4,5-tetrahydrobenzoxathiepinyl or 2,3,4,5-tetrahydrobenzodithiepinyl, and $alk_1$ and $alk_2$ are identical or different lower alkylene radicals, and their salts, especially their pharmaceutically acceptable salts.

The invention relates more especially to compounds of formula I wherein $R_1$ and $R_2$, independently of one another, are hydrogen, $C_1$–$C_4$alkyl, such as methyl, $C_1$–$C_4$alkoxy, such as methoxy, or halogen having an atomic number of up to and including 35, such as chlorine, $R_3$ is hydrogen or $C_1$–$C_7$alkyl, preferably $C_1$–$C_4$alkyl, such as, especially, methyl or, secondly, ethyl, propyl, isopropyl or butyl, the benzoheterocyclyl radical of formula Ia is 2,3-dihydrobenzofuranyl, such as 2,3-dihydrobenzofuran-2-yl, 2,3-dihydrobenzothienyl, such as 2,3-dihydrobenzothien-2-yl, chromanyl, such as chroman-3-yl, thiochromanyl, such as thiochroman-3-yl, 1,4-benzodioxanyl, such as 1,4-benzodioxan-2-yl, 1,4-benzoxathianyl, such as 1,4-benzoxathian-2-yl or -3-yl, 1,4-benzodithianyl, such as 1,4-benzodithian-2-yl, 2,3,4,5-tetrahydrobenzoxepinyl, such as 2,3,4,5-tetrahydrobenzoxepin-2-yl, -3-yl or -4-yl, 2,3,4,5-tetrahydrobenzothiepinyl, such as 2,3,4,5-tetrahydrobenzothiepin-2-yl, -3-yl or -4-yl, 2,3,4,5-tetrahydrobenzodioxepinyl, such as 2,3,4,5-tetrahydrobenzodioxepin-2-yl, -3-yl or -4-yl, 2,3,4,5-tetrahydrobenzoxathiepinyl, such as 2,3,4,5-tetrahydrobenzoxathiepin-2-yl, -3-yl or -4-yl, or 2,3,4,5-tetrahydrobenzodithiepinyl, such as 2,3,4,5-tetrahydrobenzodithiepin-2-yl, -3-yl or -4-yl, and $alk_1$ and $alk_2$ are identical or different $C_1$–$C_4$alkylene radicals, in the case of $alk_1$ especially $C_1$–$C_4$alkylene, such as methylene, ethylene, 1,3-propylene or 1,4-butylene, and in the case of $alk_2$ especially $C_2$–$C_3$alkylene, such as ethylene or, secondly, 1,3-propylene, and their salts, especially their pharmaceutically acceptable salts.

The invention relates very especially to compounds of formula I wherein $R_1$ and $R_2$, independently of one another, are hydrogen, $C_1$–$C_4$alkyl, such as methyl, $C_1$–$C_4$alkoxy, such as methoxy, or halogen having an atomic number of up to and including 35, such as chlorine, $R_3$ is hydrogen or $C_1$–$C_4$alkyl, such as, especially, methyl or, secondly, ethyl or propyl, the benzoheterocyclyl radical of formula Ia is 2,3-dihydrobenzofuranyl, such as 2,3-dihydrobenzofuran-2-yl, 2,3-dihydrobenzothienyl, such as 2,3-dihydrobenzothien-2-yl, chromanyl, such as chroman-3-yl, thiochromanyl, such as thiochroman-3-yl, 1,4-benzodioxanyl, such as 1,4-benzodioxan-2-yl, 1,4-benzodithianyl, such as 1,4-benzodithian-2-yl, 2,3,4,5-tetrahydrobenzoxepinyl, such as 2,3,4,5-tetrahydrobenzoxepin-2-yl, -3-yl or -4-yl, 2,3,4,5-tetrahydrobenzothiepinyl, such as 2,3,4,5-tetrahydrobenzothiepin-2-yl, -3-yl or -4-yl, or 2,3,4,5-tetrahydrobenzodioxepinyl, such as 2,3,4,5-tetrahydrobenzodioxepin-2-yl or -3-yl, 2,3,4,5-tetrahydrobenzoxathiepinyl, or 2,3,4,5-tetrahydrobenzodithiepinyl, such as 2,3,4,5-tetrahydrobenzodithiepin-2-yl or -3-yl, $alk_1$ is $C_1$–$C_4$alkylene, such as methylene, ethylene or 1,3-propylene, and $alk_2$ is $C_2$–$C_3$alkylene, such as ethylene, and their salts, especially their pharmaceutically acceptable salts.

The invention relates most especially to compounds of formula I wherein $R_1$ is hydrogen, $C_1$–$C_4$alkyl, such as methyl, $C_1$–$C_4$alkoxy, such as methoxy, or halogen having an atomic number of up to and including 35, such as chlorine, $R_2$ is hydrogen, $R_2$ is hydrogen or $C_1$–$C_4$alkyl, such as, especially, methyl or, secondly, ethyl, the benzoheterocyclyl radical of formula Ia is 2,3-dihydrobenzofuranyl, such as 2,3-dihydrobenzofuran-2-yl, chromanyl, such as chroman-3-yl, or 1,4-benzodioxanyl, such as 1,4-benzodioxan-2-yl, $alk_1$ is $C_1$–$C_3$alkylene, such as methylene, ethylene or 1,3-propylene, and $alk_2$ is ethylene, and their salts, especially their pharmaceutically acceptable salts.

The invention relates specifically to the compounds mentioned in the Examples and their salts, especially their pharmaceutically acceptable salts.

The invention relates further to a process, based on methods known per se, for the preparation of the compounds according to the invention, which process comprises a) in a compound of formula II

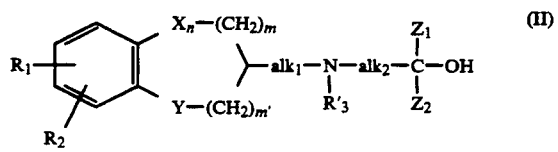

wherein $R_1$, $R_2$, n, m, m', X, Y, $alk_1$ and $alk_2$ are as defined above, $R'_3$ is one of the groups $R_3$ mentioned above or is an amino-protecting group $R_0$, $Z_1$ is a functionally modified phosphono group and $Z_2$ is a free or functionally modified phosphono group, converting functionally modified phosphono $Z_1$ and, where appropriate, $Z_2$ into the free phosphono group, or b) reacting with one another compounds of formulae IIIa and IVa

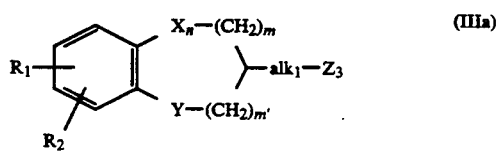

and

-continued

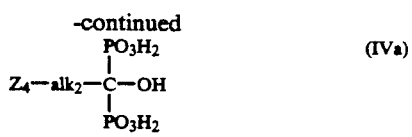
(IVa)

wherein $R_1$, $R_2$, n, m, m', X, Y, $alk_1$ and $alk_2$ are as defined above, one of the radicals $Z_3$ and $Z_4$ is a reactive esterified hydroxy group and the other is a group of the formula $-N(R'_3)-H$ wherein $R'_3$ is one of the groups $R_3$ mentioned above or is an amino-protecting group $R_0$, or the salts thereof, or, under reducing conditions, reacting with one another compounds of formulae IIIb and IVb

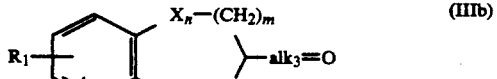
(IIIb)

and

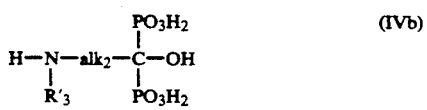
(IVb)

wherein $alk_3$ is a double-bonded radical corresponding to the radical $alk_1$, that is to say, a lower alkanylylidene radical, $R'_3$ is one of the groups $R_3$ mentioned above or is an amino-protecting group $R_0$, and $R_1$, $R_2$, n, m, m', X, Y, $alk_1$ and $alk_2$ are as defined above, or c) reacting a compound of formula V

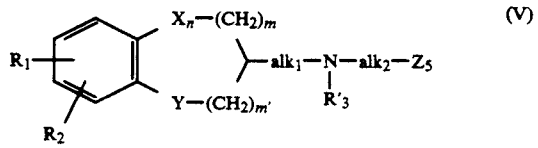
(V)

wherein $Z_5$ is carboxy, carbamoyl or cyano and $R'_3$ is one of the groups $R_3$ mentioned above or is an amino-protecting group $R_0$, and $R_1$, $R_2$, n, m, m', X, Y, $alk_1$ and $alk_2$ are as defined above, with a phosphorylating agent, hydrolysing the primary product and, in an intermediate of formula Va

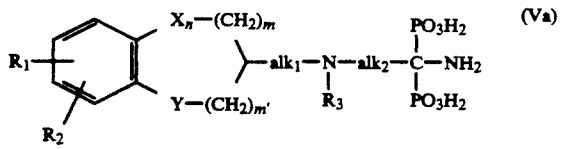
(Va)

obtained starting from compounds of formula V wherein $Z_5$ is cyano or carbamoyl, or in a salt thereof, replacing the amino group with hydroxy by treatment with nitrous acid, in each case removing the amino-protecting group $R_0$, if present, and, if desired, converting a resulting compound into a different compound of formula I, separating a mixture of isomers obtainable in accordance with the process into the components and separating the preferred isomer, and/or converting a free compound obtainable in accordance with the process into a salt or converting a salt obtainable in accordance with the process into the corresponding free compound.

The reactions of the process and the preparation of novel starting materials and intermediates are carried out by analogy with the mode of reaction and formation of known starting materials and intermediates. In those reactions, even when not expressly mentioned below, the customary auxiliaries, such as catalysts, condensation and solvolysis agents and/or solvents and diluents, and the customary reaction conditions, such as temperature and pressure conditions, and, if desired, protecting gases, are used.

Suitable amino-protecting groups $R_0$ are, for example, unsubstituted or substituted α-aralkyl-carbonyl, such as benzyl-carbonyl or benzyloxy-carbonyl groups, esterified or etherified hydroxymethyl groups, such as pivaloyloxymethyl, methoxymethyl, 2-chloroethoxymethyl or benzyloxymethyl, tetrahydropyranyl or tri-lower alkylsilyl, such as trimethylsilyl. The protecting group is introduced, for example, by reaction of the compound to be protected with a corresponding halogen derivative or with chloroiodomethane ($Cl-CH_2I$), an alkali metal, for example sodium, pivalate, methanolate, 1,2-dichloroethanolate or benzylalcoholate, or with dihydropyran.

Functionally modified phosphono groups to be converted into phosphono in accordance with process variant a) are, for example, in the form of an ester, especially in the form of a diester of the formula $-P(=O)(OR)_2$ (IIa) wherein OR is etherified hydroxy, especially lower alkoxy or lower alkanoyloxy-lower alkoxy, or a phenoxy-lower alkoxy or α-phenyl-lower alkoxy group or silyloxy, each of which is unsubstituted or substituted by lower alkyl, lower alkoxy, halogen, trifluoromethyl and/or by hydroxy, such as tri-lower alkylsilyloxy.

The conversion of functionally modified phosphono groups into free phosphono groups is carried out in customary manner, such as by hydrolysis, for example in the presence of a mineral acid, such as hydrochloric or sulfuric acid, at from approximately 80° C. to approximately 110° C., for example at boiling temperature, or by reaction with a tri-lower alkylhalosilane, for example with trimethylchlorosilane or, especially, trimethyliodosilane or trimethylbromosilane, preferably in methylene chloride in a temperature range of from approximately 0° C. to approximately 40° C., and subsequent treatment with water. α-Phenyl-lower alkyl esters can also be converted into compounds of formula I by hydrogenolysis, for example reaction with hydrogen in the presence of a hydrogenation catalyst, such as a nickel or noble metal catalyst, for example palladium-on-carbon, preferably in a lower alkanol under normal temperature and pressure conditions.

The starting materials of formula II can be prepared, for example, by condensing a compound of formula IIb

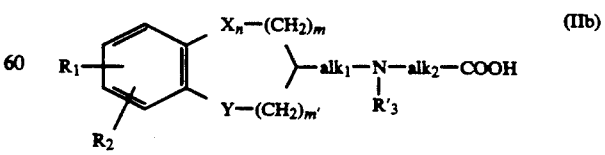
(IIb)

wherein $R_1$, $R_2$, n, m, m', X, Y, $alk_1$ and $alk_2$ are as defined above and $R'_3$ is one of the groups $R_3$ mentioned above or is an amino-protecting group $R_0$, or the anhydride or acid chloride thereof, for example at from 0° C.

to approximately 60° C., with a corresponding phosphorous acid triester of the formula P(OR)$_3$ (IIc) to form a compound of formula (IId)

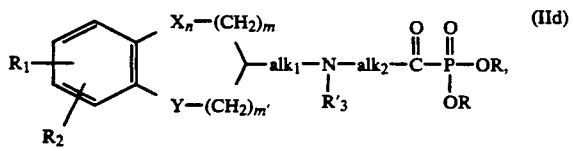

and reacting the latter further with a phosphorous acid diester of the formula H—P(=O)(OR)$_2$ (IIe) or P(OH)(OR)$_2$ (IIf) in the presence of a di-lower alkylamine, for example diethylamine, or of an alkali metal lower alkanolate, for example sodium methanolate, to form the corresponding compound of formula IIg

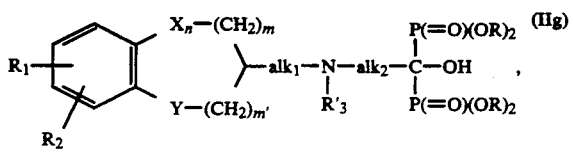

removing the amino-protecting group R$_0$, if present, and/or, if desired, introducing a radical R$_3$ other than hydrogen, for example as described below under b).

Starting materials of formula IIb, if they are not known, can be prepared, for example, by reacting a corresponding compound of formula (IIh)

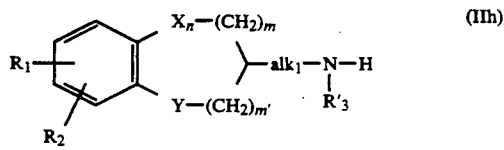

wherein R'$_3$ is a group R$_3$ or an amino-protecting group R$_0$, with a compound of the formula Z$_6$-alk$_2$-COOR (IIi) wherein Z$_6$ is halogen, such as bromine, or, for the preparation of compounds IIb wherein alk$_2$ is 1,2-lower alkylene, for example ethylene, with a compound of the formula alk$_0$-COOR (IIj) wherein alk$_0$ is lower alk-1-enyl, in each case hydrolysing the resulting ester to form the acid, removing an amino-protecting group, if present, and, if necessary or if desired, lower alkylating the freed amino group.

Reactive esters IIIa and IVa to be used in accordance with process variant b) have as reactive esterified hydroxy groups, for example, a halogen atom, such as a chlorine, bromine or iodine atom, or a sulfonyloxy group, for example methanesulfonyloxy or p-toluenesulfonyloxy.

The reaction with the mentioned reactive esters is effected, for example, in the presence of a base, such as an alkali metal or alkaline earth metal hydroxide, for example sodium hydroxide, or of a quaternary ammonium hydroxide, for example tetrabutylammonium hydroxide, advantageously in the presence of a solvent or diluent, for example a lower alkanol, a di-lower alkyl ketone or a cycloaliphatic ether, for example isopropanol, methyl ethyl ketone, dioxane or tetrahydrofuran.

The reaction of oxo compounds IIIb with aminoalkanediphosphonic acids IVb is carried out, for example, in the presence of an alkali metal borohydride, for example sodium cyanoborohydride, or, especially, by treatment with formic acid.

The starting materials of formula IVa can be prepared, for example, by reacting a compound of the formula Z$_4$-alk$_2$-Z$_5$ (IVc) wherein Z$_4$ is as defined for formula IVa and Z$_5$ is as defined for formula V, Z$_4$ preferably being halogen, such as bromine, or, for the preparation of compounds of formula V wherein alk$_2$ is 1,2-lower alkylene, for example ethylene, a compound of the formula alk$_0$-Z$_5$ (IVd) wherein alk$_0$ is a lower alk-1-enyl radical, in customary manner, for example in chlorobenzene, with phosphorous acid and phosphorus trichloride or with phosphoric acid and an excess of phosphorus tribromide, and then working up by hydrolysis. Starting materials IVb can be prepared analogously by reacting compounds of the formula R$_0$-N(R'$_3$)-alk$_2$-Z$_5$ (IVe) with phosphorous acid and phosphorus trichloride, R$_0$ being a customary amino-protecting group.

Suitable phosphorylating agents for process variant c) are, for example, phosphorus trioxide, phosphorus trihalides in admixture with phosphorous acid or phosphoric acid, phosphorus oxychloride or phosphorus pentachloride, or phosphorus trichloride in admixture with chlorine. Preference is given to phosphorus trioxide, which is preferably formed in situ by reaction of phosphorus trichloride with phosphorous acid, or to the phosphorous acid component, which is preferably formed in situ by reaction with an excess of phosphorus trichloride with aqueous phosphoric acid, for example with commercially available, approximately 75% to 95%, preferably approximately 85%, phosphoric acid. The reaction is advantageously carried out with heating, for example at approximately from 70° to 120° C., in a suitable solvent, such as tetrachloroethane, trichloroethane, chlorobenzene, chlorotoluene or paraffin oil, and with hydrolytic working-up.

The treatment of intermediates of formula Va with nitrous acid is effected in customary manner with the release of the latter in aqueous solution from one of its salts, for example from sodium nitrite, by treatment with an acid, for example the action of hydrochloric acid, there being formed as intermediate a corresponding unstable diazonium salt, for example a chloride, which removes nitrogen with the introduction of the α-hydroxy group.

The starting materials of formula V, if they are not known, can be prepared, for example, by reacting a corresponding compound of formula (IIh)

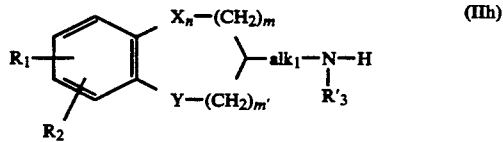

with a compound of the formula Z$_4$-alk$_2$-Z$_5$ (IVc) wherein Z$_4$ is as defined for formula IVa and Z$_5$ is as defined for formula V, Z$_4$ preferably being halogen, such as bromine, or, for the preparation of compounds of formula V wherein alk$_2$ is 1,2-lower alkylene, for example ethylene, with a compound of the formula alk$_0$-Z$_5$ (IVd) wherein alk$_0$ is a lower alk-1-enyl radical, in each case removing the amino-protecting group, if present, and, if desired, hydrolysing the resulting primary product in each case to form the acid.

Compounds obtainable in accordance with the process can be converted in customary manner into different compounds of formula I.

For example, in compounds of formula I wherein $R_3$ is hydrogen, lower alkyl $R_3$ can be introduced in customary manner by reaction with a reactive ester of the formula $R_3$-$Z_6$ (IX) wherein $R_3$ is lower alkyl and $Z_6$ is reactive esterified hydroxy, for example a halogen atom, such as a chlorine, bromine or iodine atom, or a sulfonyloxy group, for example methanesulfonyloxy or p-toluenesulfonyloxy, or by reaction with a lower alkanal or a di-lower alkyl ketone of the formula $R_3{=}O$ (IXa) under reducing conditions.

The reaction with the mentioned reactive esters (IX) is effected, for example, in the presence of a base, such as an alkali metal or alkaline earth metal hydroxide, for example sodium hydroxide, or a quaternary ammonium hydroxide, for example tetrabutylammonium hydroxide, advantageously in the presence of a solvent or diluent, for example a lower alkanol, a di-lower alkyl ketone or a cycloaliphatic ether, for example isopropanol, methyl ethyl ketone, dioxane or tetrahydrofuran. The reaction with oxo compounds (IXa) is carried out, for example, in the presence of an alkali metal borohydride, for example sodium cyanoborohydride, or, especially, by treatment with formic acid. In a preferred form, a corresponding compound of formula Ia can be substituted by a lower alkyl radical $R_3$ under reducing conditions by using a lower alkanal, for example formaldehyde, and formic acid.

It is also possible to introduce groups $R_1$ and/or $R_2$ other than hydrogen into the benzo moiety of the benzoheterocyclyl radical of compounds of formula I; lower alkyl, for example, by reaction with a lower alkyl halide in the presence of aluminium trichloride; lower alkoxy, for example, by nitration, reduction of the nitro group to the amino group, diazotisation of the latter and treatment of the resulting diazonium salt with the corresponding lower alkanol, with heating; and halogen, for example, by treatment with chlorine or bromine, advantageously in the presence of a Lewis acid, for example iron-III chloride. It is, however, also possible to replace halogen with trifluoromethyl, for example by treatment with trifluoroiodomethane in the presence of copper powder or copper-I iodide.

Depending upon the starting materials and procedures chosen, the novel compounds may be in the form of one of the possible isomers, for example, depending on the number of asymmetric carbon atoms, in the form of optical isomers, such as in the form of an enantiomer, such as an antipode and/or a diastereoisomer, or in the form of mixtures thereof, such as mixtures of enantiomers, for example racemates, mixtures of diastereoisomers or mixtures of racemates.

Resulting mixtures of diastereoisomers and mixtures of racemates can be separated in known manner into the pure diastereoisomers or racemates on the basis of the physico-chemical differences between the constituents, for example by chromatography and/or fractional crystallisation. Furthermore, resulting racemates can be separated into the optical antipodes by known methods, for example by recrystallisation from an optically active solvent, with the aid of microorganisms or by reaction of a compound of formula I or of an anhydride thereof with an optically active base or with an optically active alcohol and separation of the resulting diastereoisomeric esters, for example on the basis of their different solubilities, into the diastereoisomers from which the enantiomers can be freed by the action of suitable agents. Racemates of formula I can also be separated by reaction with an optically active base into mixtures of the diastereoisomeric salts, and separation thereof into the diastereoisomers from which the enantiomers can be freed in customary manner.

Optically active bases customarily used for that purpose are, for example, optically active alkaloids, such as quinine, cinchonine, brucine and the like, or, especially, α-phenylethylamine.

Furthermore, resulting salt-forming compounds can be converted in a manner known per se into salts, for example by reaction of a solution of the free compound in a suitable solvent or mixture of solvents with a corresponding base or with a suitable ion exchanger.

Resulting salts can be converted into the free compounds in a manner known per se, for example by treatment with an acid, such as a mineral acid, for example hydrochloric acid.

Resulting salts can be converted into different salts in a manner known per se, for example by treatment with a suitable base, such as sodium hydroxide or potassium hydroxide, ammonia or a suitable amine.

The compounds of formula I, including their salts, may also be obtained in the form of hydrates or may include the solvent used for crystallisation.

In view of the close relationship between the novel compounds in free form and in the form of their salts, hereinbefore and hereinafter any reference to the free compounds or their salts should be understood as including the corresponding salts or free compounds, as appropriate and expedient.

The invention relates also to those forms of the process in which a compound obtainable as intermediate at any stage of the process is used as starting material and the remaining steps are carried out, or in which a starting material is used in the form of a salt or, especially, is formed under the reaction conditions.

The invention relates also to the novel starting materials developed specifically for the preparation of the compounds of the invention, especially to those starting materials resulting in the compounds of formula I that were described at the beginning as being preferred, to processes for the preparation thereof and to their use as intermediates.

The novel compounds of formula I can be used, for example, in the form of pharmaceutical compositions that comprise a therapeutically effective amount of the active ingredient, optionally together with inorganic or organic, solid or liquid pharmaceutically acceptable carriers that are suitable for enteral, for example oral, or parenteral administration. There are used, for example, tablets or gelatin capsules that comprise the active ingredient together with diluents, for example lactose, dextrose, saccharose, mannitol, sorbitol, cellulose and/or lubricants, for example silica, talc, stearic acid or salts thereof, such as magnesium or calcium stearate, and/or polyethylene glycol. Tablets can also comprise binders, for example magnesium aluminium silicate, starches, such as corn, wheat, rice or arrowroot starch, gelatin, tragacanth, methylcellulose, sodium carboxymethylcellulose and/or polyvinylpyrrolidone, and, if desired, disintegrators, for example starches, agar, alginic acid or a salt thereof, for example sodium alginate, and/or effervescent mixtures, or absorbents, colouring agents, flavourings and sweeteners. The novel compounds of formula I can also be used in the form of parenterally administrable compositions or in the form of infusion solutions. Such solutions are preferably isotonic aqueous solutions or suspensions which, for example in the case of lyophilised compositions that comprise the active ingredient on its own or together with a carrier, for example mannitol, can be prepared before use. The pharmaceutical compositions may be sterilised and/or may comprise excipients, for example preservatives, stabilisers, wetting agents and/or emulsifiers, solubilisers, salts for regulating the osmotic pressure and/or buffers. The pharmaceutical compositions in question, which, if desired, may comprise further pharmacologically active substances, are prepared in a manner known per se, for example by means of conventional mixing, granulating, confectioning, dissolving or lyophilising processes, and comprise approximately from 0.1% to 100%, especially from approximately 1% to approximately 50%, in the case of lyophilisates up to approximately 100%, active ingredient.

Suitable for parenteral administration are especially aqueous solutions of an active ingredient in water-soluble form, for example in the form of a water-soluble pharmaceutically acceptable salt, and also suspensions of active ingredient, such as oily injection suspensions, there being used suitable lipophilic solvents or vehicles, such as fatty oils, for example sesame oil, or synthetic fatty acid esters, for example ethyl oleate, or triglycerides, or aqueous injection suspensions that comprise viscosity-increasing substances, for example sodium carboxymethylcellulose, sorbitol and/or dextran, and, optionally, stabilisers.

The invention relates further to the use of compounds of formula I for the treatment of diseases that can be attributed to calcium metabolism disorders, preferably by providing pharmaceutical compositions. The dose of a compound of formula I according to the invention can depend upon various factors, such as the mode of administration, the species, age and/or individual condition. Single doses comprise, for example, in the case of parenteral administration, from approximately 0.01 to approximately 0.1 mg, preferably from 0.02 to 0.08 mg, and, in the case of oral administration, from approximately 0.2 to approximately 2.5 mg, preferably from 0.3 to 1.5 mg, per kilogram of body weight. The preferred single doses are therefore approximately from 0.5 to 5.0 mg in the case of parenteral administration, and approximately from 10 to 100 mg in the case of oral administration. The daily doses to be administered are, in the case of oral administration, from approximately 0.25 to approximately 10 mg/kg, and in the case of warm-blooded animals having a body weight of approximately 70 kg, they are preferably from approximately 20 mg to approximately 500 mg.

The following Examples illustrate the invention; temperatures are given in degrees Celsius and pressures in mbar.

EXAMPLE 1

5.0 g (0.0175 mol) of 3-{N-[2-(chroman-3-yl)ethyl]amino}propionic acid hydrochloride are heated under reflux at 100°, with stirring, with 2.4 ml of 85% phosphoric acid and 15 ml of chlorobenzene. 4.6 ml of phosphorus trichloride are then added dropwise, with the evolution of gas occurring. In the course of 30 minutes the reaction mixture deposits a thick mass. Heating is continued for 2 hours at 100° and then the supernatant chlorobenzene is decanted off. The viscous mass that remains is heated under reflux at boiling point with stirring for 3 hours with 40 ml of 4N hydrochloric acid. The reaction mixture is filtered hot with the addition of carbon and the filtrate is concentrated under reduced pressure to a syrupy consistency. When acetone is added, 3-{N-[2-(chroman-3-yl)ethyl]amino}-1-hydroxypropane-1,1-diphosphonic acid having a melting point of 187°-192° (decomposition) crystallises out.

The starting material can be prepared, for example, as follows: 3.0 g (0.01 mol) of 3-{N-[2-(chroman-3-yl)ethyl]amino}propionic acid methyl ester hydrochloride are heated at boiling point for 4 hours, with stirring, with 20 ml of 4N hydrochloric acid. The reaction mixture is then concentrated by evaporation under reduced pressure and the residue is stirred with acetone, yielding 3-{N-[2-(chroman-3-yl)ethyl]amino}propionic acid hydrochloride having a melting point of 186°-188°.

EXAMPLE 2

4.1 g (0.010 mol) of 3-{N-[2-(chroman-3-yl)ethyl]amino}-1-hydroxypropane-1,1-diphosphonic acid are stirred with 20 ml of N sodium hydroxide solution and 4.0 ml of a 37% aqueous formaldehyde solution, and 1.0 g of sodium cyanoborohydride is added in portions thereto. After stirring for 5 hours at 20°, 4.0 ml of 36% hydrochloric acid are added dropwise. After concentration under reduced pressure to half the volume and cooling in an ice bath, 3-{N-[2-(chroman-3-yl)ethyl]-N-methylamino}-1-hydroxypropane-1,1-diphosphonic acid having a melting point of 225°-226° (decomposition) crystallises out. It is filtered with suction and dried under reduced pressure.

EXAMPLE 3

The following compounds can also be prepared in a manner analogous to that described in Examples 1 and 2:

3-[N-(6-methoxy-1,4-benzodioxan-2-yl)methyl-N-methylamino]-1-hydroxypropane-1,1-diphosphonic acid;

3-[N-(7-chloro-1,4-benzodioxan-2-yl)methyl-N-methylamino]-1-hydroxypropane-1,1-diphosphonic acid and 3-[N-(2,3-dihydrobenzothien-2-yl)methyl-N-methylamino]-1-hydroxypropane-1,1-diphosphonic acid.

EXAMPLE 4

In a manner analogous to that described in Example 1, 3-{N-[2-(chroman-3-yl)ethyl]-N-methylamino}-1-hydroxypropane-1,1-diphosphonic acid having a melting point of 225°-226° (identical with the product according to Example 2) is obtained starting from 3-{N-[2-(chroman-3-yl)ethyl]-N-methylamino}-propionic acid hydrochloride.

The starting material can be prepared, for example, as follows:

3.0 g (0.01 mol) of 3-{N-[2-(chroman-3-yl)ethyl]amino} propionic acid methyl ester hydrochloride are suspended with stirring in 30 ml of acetonitrile, and 4.0 ml (0.05 mol) of 37% formaldehyde in water are added thereto. 0.84 g (0.01 mol) of sodium hydrogen carbonate is then added and stirring is continued, yielding a clear solution. 1.0 g of sodium cyanoborohydride is added in portions to the solution and the pH of the suspension is then adjusted to 7 by the dropwise addition of glacial acetic acid. The reaction mixture is then stirred for 1 hour at room temperature, the solvent is distilled off under reduced pressure and the oily residue is partitioned between 50 ml of diethyl ether and 15 ml of N sodium hydrogen carbonate solution. The organic phase is separated off, dried over sodium sulfate and concentrated by evaporation. Purification by chromatography on a silica gel column (diameter 2 cm, length 30 cm, Kieselgel ® Merck 60) with toluene/ethanol (9:1 parts by volume) yields 3-{N-[2-(chroman-3-yl)ethyl]-N-methylamino}-propionic acid methyl ester in the form of an oil. 3-{N-[2-(chroman-3-yl)ethyl]-N-methylamino}-propionic acid hydrochloride having a melting point of 169°–170° is obtained from the latter in a manner analogous to that described in Example 1 by heating with 20 ml of 4N hydrochloric acid.

EXAMPLE 5

In a manner analogous to that described in Example 1, 3-{N-[2-(chroman-2-yl)ethyl]-N-methylamino}-1-hydroxypropane-1,1-diphosphonic acid having a melting point of 151°–155° (decomposition) is obtained starting from 3.0 g (0.01 mol) of 3-{N-[2-(chroman-2-yl)ethyl]-N-methylamino}-propionic acid methyl ester hydrochloride via 3-{N-[2-(chroman-2-yl)ethyl]-N-methylamino}-propionic acid hydrochloride having a melting point of 130°–132°.

EXAMPLE 6

In a manner analogous to that described in Example 1, there is obtained starting from 2.8 g (0.01 mol) of 3-[N-(6-methylbenzo-1,4-dioxan-2-ylmethyl)amino]propionic acid ethyl ester, after boiling under reflux for 4 hours with 20 ml of 4N hydrochloric acid, 3-[N-(6-methylbenzo-1,4-dioxan-2-ylmethyl)amino]-propionic acid hydrochloride having a melting point of 154°–156°, and, from the latter, 3-[N-(6-methylbenzo-1,4-dioxan-2-ylmethyl)amino]-1-hydroxypropane-1,1-diphosphonic acid having a melting point of 183°–184° (decomposition).

The starting material can be prepared, for example, as follows:

4.4 ml (0.04 mol) of ethyl acrylate are added to 7.2 g (0.04 mol) of 6-methylbenzo-1,4-dioxan-2-ylmethylamine and the reaction mixture is left to stand for 60 hours at room temperature, yielding crude 3-[N-(6-methylbenzo-1,4-dioxan-2-ylmethyl)amino]-propionic acid ethyl ester which can be used without further purification.

EXAMPLE 7

In a manner analogous to that described in Example 1, 3-[N-(benzo-1,4-dioxan-2-ylmethyl)-N-methylamino]-1-hydroxypropane-1,1-diphosphonic acid having a melting point of 176°–180° (decomposition) is obtained starting from 3-[N-(benzo-1,4-dioxan-2-ylmethyl)-N-methylamino]-propionic acid hydrochloride.

EXAMPLE 8

In a manner analogous to that described in Example 1, there is obtained starting from 2.8 g (0.01 mol) of 3-[N-(5-methoxy-2,3-dihydrobenzofuran-2-yl)methylamino]-propionic acid ethyl ester by heating with hydrochloric acid, concentrating by evaporation and triturating with acetone, 3-[N-(5-methoxy-2,3-dihydrobenzofuran-2-yl)methylamino]-propionic acid hydrochloride having a melting point of 150°–154°, and, from the latter, 3-[N-(5-methoxy-2,3-dihydrobenzofuran-2-yl)methylamino]-1-hydroxypropane-1,1-diphosphonic acid having a melting point of 157°–161° (decomposition).

The starting material can be prepared, for example, as follows:

4.4 ml (0.04 mol) of ethyl acrylate are added to 6.5 g (0.04 mol) of 5-methoxy-2,3-dihydrobenzofuran-2-ylmethylamine and the reaction mixture is left to stand for 60 hours at room temperature, yielding 3-[N-(5-methoxy-2,3-dihydrobenzofuran-2-yl)methylamino]-propionic acid ethyl ester in the form of a yellowish oil.

EXAMPLE 9

In a manner analogous to that described in Example 2, 3-[N-(6-methylbenzo-1,4-dioxan-2-ylmethyl)-N-methylamino]-1-hydroxypropane-1,1-diphosphonic acid having a melting point of 175°–178° (decomposition) is obtained starting from 3-[N-(6-methylbenzo-1,4-dioxan-2-yl)methylamino]-1-hydroxypropane-1,1-diphosphonic acid.

EXAMPLE 10

In a manner analogous to that described in Example 1, there is obtained starting from 7.0 g (0.022 mol) of 3-[N-(6-chlorobenzo-1,4-dioxan-2-ylmethyl)-N-methylamino]-propionic acid ethyl ester by heating with hydrochloric acid, concentrating by evaporation and triturating with acetone, 3-[N-(6-chlorobenzo-1,4-dioxan-2-ylmethyl)-N-methylamino]-propionic acid hydrochloride having a melting point of 122°–125°, and, from the latter, 3-[N-(6-chlorobenzo-1,4-dioxan-2-ylmethyl)-N-methylamino]-1-hydroxypropane-1,1-diphosphonic acid having a melting point of 174°–176° (decomposition).

The starting material can be prepared, for example, as follows:

14.8 g (0.0675 mol) of 6-chloro-2-chloromethylbenzo-1,4-dioxane and 31.0 g of methylamine are heated in a pressure tube for 24 hours at 120°. Evaporating off the excess methylamine and distilling under reduced pressure yield 6-chloro-2-methylaminomethylbenzo-1,4-dioxane having a boiling point of 70°–73° (at 0.001 mbar).

3.3 ml (0.03 mol) of ethyl acrylate are added to 5.0 g (0.023 mol) of 6-chloro-2-methylaminomethylbenzo-1,4-dioxane and the reaction mixture is allowed to stand for 60 hours at room temperature, yielding crude 3-[N-(6-chlorobenzo-1,4-dioxan-2-ylmethyl)-N-methylamino]-propionic acid ethyl ester which can be used without further purification.

EXAMPLE 11

Tablets, each comprising 50 mg of 3-{N-[2-(chroman-3-yl)ethyl]-N-methylamino}-1-hydroxypropane-1,1-diphosphonic acid or a salt, for example the disodium salt, thereof, can be prepared as follows:

| Composition (10 000 tablets) | |
|---|---|
| active ingredient | 500.0 g |
| lactose | 500.0 g |
| potato starch | 325.0 g |
| gelatin | 8.0 g |
| talc | 60.0 g |
| magnesium stearate | 10.0 g |
| silica (highly dispersed) | 20.0 g |
| ethanol | q.s. |

The active ingredient is mixed with the lactose and 292 g of potato starch, and the mixture is moistened with an ethanolic solution of the gelatin and granulated through a sieve. After drying, the remaining potato starch, the talc, the magnesium stearate and the silica are mixed in and the mixture is compressed to form tablets which each weigh 145.0 mg and comprise 50.0 mg of active ingredient, and which may, if desired, be provided with breaking notches for finer adaptation of the dose.

EXAMPLE 12

Film-coated tablets, each comprising 100 mg of 3-{N-[2-(chroman-3-yl)ethyl]-N-methylamino}-1-hydroxypropane-1,1-diphosphonic acid or a salt, for example the disodium salt, thereof, can be prepared as follows:

| Composition (for 1000 film-coated tablets) | |
|---|---|
| active ingredient | 100.0 g |
| lactose | 100.0 g |
| corn starch | 70.0 g |
| talc | 8.5 g |
| calcium stearate | 1.5 g |
| hydroxypropylmethylcellulose | 2.36 g |
| shellac | 0.64 g |
| water | q.s. |
| methylene chloride | q.s. |

The active ingredient, the lactose and 40 g of the corn starch are mixed, and the mixture is moistened with a paste, prepared from 15 g of the corn starch and water (with heating), and granulated. The granules are dried, the remaining corn starch, the talc and the calcium stearate are added and mixed with the granules. The mixture is compressed to form tablets (weight: 280 mg), which are coated with a solution of the hydroxypropylmethylcellulose and the shellac in methylene chloride; final weight of the film-coated tablet: 283 mg.

EXAMPLE 13

Gelatin dry-filled capsules, containing 100 mg of active ingredient, for example 3-{N-[2-(chroman-3-yl)ethyl]-N-methylamino}-1-hydroxypropane-1,1-diphosphonic acid or a salt, for example the disodium salt, thereof, can be prepared, for example, as follows:

| Composition (for 1000 capsules) | |
|---|---|
| active ingredient | 100.0 g |
| microcrystalline cellulose | 30.0 g |
| sodium lauryl sulfate | 2.0 g |
| magnesium stearate | 8.0 g |

The sodium lauryl sulfate is added to the lyophilised active ingredient through a sieve having a mesh size of 0.2 mm. The two components are intimately mixed. Then the microcrystalline cellulose is added through a sieve having a mesh size of 0.9 mm. The mixture is again intimately mixed for 10 minutes. Finally, the magnesium stearate is added through a sieve having a mesh size of 0.8 mm. After further mixing for 3 minutes, gelatin dry-fill capsules of size 0 are each filled with 390 mg of the resulting formulation.

EXAMPLE 14

A 0.2% injection or infusion solution of 3-{N-[2-(chroman-3-yl)ethyl]-N-methylamino}-1-hydroxypropane-1,1-diphosphonic acid or of a salt, for example the disodium salt, thereof can be prepared, for example, as follows:

| Composition (for 1000 ampoules) | |
|---|---|
| active ingredient | 5.0 g |
| sodium chloride | 22.5 g |
| phosphate buffer pH = 7.4 | 300.0 g |
| demineralised water | ad 2500.0 ml |

The active ingredient is dissolved in 1000 ml of water and filtered through a micro-filter. The buffer solution is added, and the mixture is made up to 2500 ml with water. To prepare unit dose forms, 1.0 or 2.5 ml are introduced into each glass or plastics ampoule, which then contains 2.0 or 5.0 mg, respectively, of active ingredient.

EXAMPLE 15

In a manner analogous to that described in Examples 11 to 14, it is also possible to prepare pharmaceutical compositions comprising a different compound of formula I according to any one of Examples 1 to 10.

What is claimed is:

1. A benzoheterocyclylalkylaminoalkanediphosphonic acid of formula I

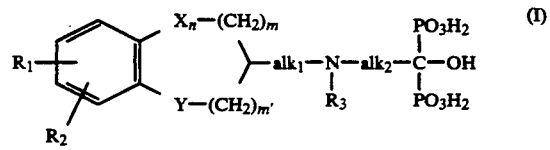

wherein $R_1$ and $R_2$, independently of one another, are hydrogen, lower alkyl, lower alkoxy, halogen or trifluoromethyl, $R_3$ is hydrogen or lower alkyl, X and Y, independently of one another, are oxy or thio, $alk_1$ and $alk_2$ are identical or different lower alkylene radicals, n is 0 or 1 and m and m', independently of one another, are 0, 1 or 2, the sum of n, m and m' being 1, 2 or 3, or a salt thereof.

2. A compound according to claim 1 of formula I wherein $R_1$ and $R_2$, independently of one another, are hydrogen, lower alkyl, lower alkoxy, halogen or trifluoromethyl, $R_3$ is hydrogen or lower alkyl, the benzoheterocyclyl radical of formula

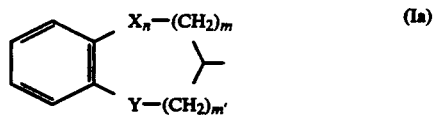

is 2,3-dihydrobenzofuranyl, 2,3-dihydrobenzothienyl, chromanyl, thiochromanyl, 1,4-benzodioxanyl, 1,4-benzoxathianyl, 1,4-benzodithianyl, 2,3,4,5-tetrahydrobenzoxepinyl, 2,3,4,5-tetrahydrobenzothiepinyl, 2,3,4,5-tetrahydrobenzodioxepinyl, 2,3,4,5-tetrahydrobenzoxathiepinyl or 2,3,4,5-tetrahydrobenzodithiepinyl and $alk_1$ and $alk_2$ are identical or different lower alkylene radicals, or a salt thereof.

3. A compound according to claim 1 of formula I wherein $R_1$ and $R_2$, independently of one another, are hydrogen, lower alkyl, lower alkoxy, halogen or trifluoromethyl, $R_3$ is hydrogen or lower alkyl, the benzoheterocyclyl radical of formula

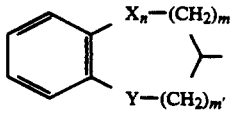

is 2,3-dihydrobenzofuranyl, chromanyl or 1,4-benzodioxanyl and $alk_1$ and $alk_2$ are identical or different lower alkylene radicals, or a salt thereof.

4. A compound according to claim 1 of formula I wherein $R_1$ and $R_2$, independently of one another, are hydrogen, $C_1$-$C_4$alkyl, $C_1$-$C_4$alkoxy or halogen having an atomic number of up to and including 35, $R_3$ is hydrogen or $C_1$-$C_7$alkyl, the benzoheterocyclyl radical of formula Ia is 2,3-dihydrobenzofuranyl, 2,3-dihydrobenzothienyl, chromanyl, thiochromanyl, 1,4-benzodioxanyl, 1,4-benzoxathianyl, 1,4-benzodithianyl, 2,3,4,5-tetrahydrobenzoxepinyl, 2,3,4,5-tetrahydrobenzothiepinyl, 2,3,4,5-tetrahydrobenzodioxepinyl, 2,3,4,5-tetrahydrobenzoxathiepinyl or 2,3,4,5-tetrahydrobenzodithiepinyl and $alk_1$ and $alk_2$ are identical or different $C_1$-$C_4$alkylene radicals, or a salt thereof.

5. A compound according to claim 1 of formula I wherein $R_1$ and $R_2$, independently of one another, are hydrogen, $C_1$-$C_4$alkyl, $C_1$-$C_4$alkoxy or halogen having an atomic number of up to and including 35, $R_3$ is hydrogen or $C_1$-$C_4$alkyl, the benzoheterocyclyl radical of formula Ia is 2,3-dihydrobenzofuranyl, chromanyl or 1,4-benzodioxanyl, $alk_1$ is $C_1$-$C_4$alkylene and $alk_2$ is $C_2$-$C_3$alkylene, or a salt thereof.

6. A compound according to claim 1 of formula I wherein $R_1$ is hydrogen, $C_1$-$C_4$alkyl, $C_1$-$C_4$alkoxy or halogen having an atomic number of up to and including 35, $R_2$ is hydrogen, $R_3$ is hydrogen or $C_1$-$C_4$alkyl, the benzoheterocyclyl radical of formula Ia is 2,3-dihydrobenzofuranyl, chromanyl or 1,4-benzodioxanyl, $alk_1$ is $C_1$-$C_3$alkylene and $alk_2$ is ethylene, or a salt thereof.

7. A compound as claimed in claim 1 being 3-{N-[2-(Chroman-3-yl)ethyl]amino}-1-hydroxypropane-1,1-diphosphonic acid or a salt thereof.

8. A compound as claimed in claim 1 being 3-{N-[2-(Chroman-3-yl)ethyl)-N-methylamino}-1-hydrozypropane-1,1-diphosphonic acid or a salt thereof.

9. A compound as claimed in claim 1 being 3-[N-(6-Methyl-1,4-benzodioxan-2-yl)methyl-N-methylamino]-1-hydroxypropane-1,1-diphosphonic acid or a salt thereof.

10. A compound as claimed in claim 1 being 3-[N-(6-Methoxy-1,4-benzodioxan-2-yl)methyl-N-methylamino]-1-hydroxypropane-1,1-diphosphonic acid or a salt thereof.

11. A compound as claimed in claim 1 being 3-[N-(7-Chloro-1,4-benzodioxan-2-yl)methyl-N-methylamino]-1-hydroxypropane-1,1-diphosphonic acid or a salt thereof.

12. A compound as claimed in claim 1 being 3-[N-(2,3-Dihydrobenzothien-2-yl)methyl-N-methylamino]-1-hydroxypropane-1,1-diphosphonic acid or a salt thereof.

13. A compound as claimed in claim 1 being 3-{N-[2-(Chroman-2-yl)ethyl]-N-methylamino}-1-hydroxypropane-1,1-diphosphonic acid or a salt thereof.

14. A compound as claimed in claim 1 being 3-[N-(6-Methylbenzo-1,4-dioxan-2-ylmethyl)amino]-1-hydroxypropane-1,1-diphosphonic acid or a salt thereof.

15. A compound as claimed in claim 1 being 3-[N-(Benzo-1,4-dioxan-2-ylmethyl)-N-methylamino]-1-hydroxypropane-1,1-diphosphonic acid or a salt thereof.

16. A compound as claimed in claim 1 being 3-[N-(5-Methoxy-2,3-dihydrobenzofuran-2-yl)methylamino]-1-hydroxypropane-1,1-diphosphonic acid or a salt thereof.

17. A compound as claimed in claim 1 being 3-[N-(6-Chlorobenzo-1,4-dioxan-2-ylmethyl)-N-methylamino]-1-hydroxypropane-1,1-diphosphonic acid or a salt thereof.

18. A pharmaceutical composition comprising an theraputically effective amount of a compound according to claim 1 in free form or in the form of a pharmaceutically acceptable salt, together with customary pharmaceutical excipients.

19. A method for the treatment of diseases that are attributed to calcium metabolism disorders, of inflammatory processes in joints, degenerative processes in the articular cartilage, and of calcium deposits in blood vessels or in prosthetic implants, which method comprises administering an therapeutically effective amount of a compound according to claim 1 to a warm-blooded organism in need of such treatment.

20. The method of claim 19 wherein said disease is selected from the group consisting of tumor-induced hypercalceia, bone metastases, Paget's disease, osteoporosis, periodontitis, and hyperparathyroidism.

* * * * *